United States Patent [19]

Molzahn

[11] Patent Number: 5,145,987
[45] Date of Patent: Sep. 8, 1992

[54] PROCESS FOR THE PREPARATION OF CIS-1,2-TRANS-4-CYCLOHEXANE TRICARBOXYLIC ACID AND ESTERS

[75] Inventor: David C. Molzahn, Midland, Mich.

[73] Assignee: The Dow Chemical Company, Midland, Mich.

[21] Appl. No.: 703,981

[22] Filed: May 22, 1991

[51] Int. Cl.$^5$ .............................................. C07L 67/36
[52] U.S. Cl. ..................................... 560/114; 562/497
[58] Field of Search ........................ 560/114; 562/497

[56] References Cited

U.S. PATENT DOCUMENTS

| | | | |
|---|---|---|---|
| 3,437,676 | 4/1969 | Kutepow et al. | 260/468 |
| 3,444,237 | 5/1969 | Jaffe | 260/468 |
| 4,681,707 | 7/1987 | Alper | 560/114 |

OTHER PUBLICATIONS

Bittler et al., Angew. Chem. internat. Edit. 7 (1968) 329–335.
Cavinato et al., Journal of Molecular Catalysis 10 (1981) 161–170.
Alper et al., J. Chem. Soc., Chem. Commun. (1983) 1270–1271.
Fenton, J. Org. Chem. 38 (1973) 3192–3198.
James et al., JACS 98 (1976) 1810–1823.

*Primary Examiner*—Michael L. Shippen

[57] ABSTRACT

A process is disclosed for preparing cyclohexane tricarboxylic acids and esters thereof comprising contacting carbon monoxide, cis-1,2,3,6-tetrahydrophthalic acid anhydride and water or a lower alkanol at elevated pressure and temperature and in the presence of a palladium complex and an ether solvent wherein the selectivity to cis-1,2-trans-4-cyclohexane tricarboxylic acids and esters thereof is greater than that obtained in the absence of the ether solvent.

6 Claims, No Drawings

PROCESS FOR THE PREPARATION OF CIS-1,2-TRANS-4-CYCLOHEXANE TRICARBOXYLIC ACID AND ESTERS

BACKGROUND OF THE INVENTION

This invention relates to the preparation of cis-1,2-trans-4-cyclohexane tricarboxylic acids and esters thereof.

It is known that olefins may be carboxylated under relatively mild conditions in the presence of palladium-phosphine complexes. See, for example, Fenton, *J. Org. Chem.*, 38 3192–3198 (1973); Bittler et al., *Angew. Chem. internat. Edit.*, 7, 329–335 (1968); and James et al. *J.A.C.S.*, 98, 1810–1823 (1976).

U.S. Pat. No. 3,444,237 to Jaffe dated May 13, 1969 is directed to a process for hydrogenating trimellitic acid to produce a mixture of the isomers of 1,2,4-cyclohexane tricarboxylic acids. This process uses a metallic ruthenium catalyst. U.S. Pat. No. 3,437,676 to Kutepow et al. dated Apr. 8, 1969 teaches that an alkene is reacted with water or phenol to produce a carboxylic acid or ester in the presence of a palladium complex.

None of these teachings address the issue of stereo selectivity.

SUMMARY OF THE INVENTION

The present invention is directed to a process for preparing cyclohexane tricarboxylic acids and esters thereof comprising contacting carbon monoxide, a first reagent selected from the group consisting of cis-1,2,3,6-tetrahydrophthalic acid, cis-1,2,3,6-tetrahydrophthalic acid ester, cis-1,2,3,6-tetrahydrophthalic acid anhydride and mixtures thereof, and a second reagent selected from the group consisting of water, lower alkanols and mixtures thereof at elevated pressure and temperature and in the presence of a palladium complex and an ether solvent wherein the selectivity to cis-1,2-trans-4-cyclohexane tricarboxylic acids and esters thereof is greater than that obtained in the absence of the ether solvent.

It is surprising that the process of the present invention results in a process selective to the desired cis-trans isomer.

The isomer so produced is useful as a crosslinker in the preparation of branched aliphatic epoxies.

DETAILED DESCRIPTION OF THE ILLUSTRATIVE EMBODIMENTS

In the process of the present invention, it has been found that the selectivity to cis-1,2-trans-4-cyclohexanetricarboxylic acids or esters (the cis-trans isomer) is increased by the use of the specified ether solvent. It is generally known that cyclic alkenes can be carboxylated under relatively mild conditions in the presence of palladium complexes with carbon monoxide at elevated temperatures and pressures. However, known methods have resulted in a mixture of regio and stereo isomers.

It has been surprisingly found that in the practice of the present invention, selectivity to the cis-trans isomer is increased by the use of an ether solvent as compared to selectivities obtained in other solvents or in the absence of solvents. Preferred ether solvents include dioxane, tetrahydropyran, bis(2-methoxyethyl) ether, bis(2-ethoxyethyl) ether, diethyl ether, ethylene glycol diethyl ether and tetrahydrofuran The starting material in the present invention is a cis-1,2,3,6-tetrahydrophthalic acid or ester or anhydride thereof. The second reagent is water or a lower alkanol or mixtures thereof. Lower alkanols are preferably $C_{1-6}$ alkanols.

The use of palladium complexes for the carboxylation of alkenes under mild conditions is known. See, e.g., Bittler et al., *Angew. Chem. internat. Edit.*, 7,329–335 (1968). In a preferred embodiment of the present invention, the palladium complex may be prepared in situ by admixing a palladium (II) salt such as palladium (II) chloride and a phosphine such as triphenylphosphine into the reaction mixture.

In addition to palladium (II) chloride, other palladium salts such as $PdBr_2$, $PdI_2$ and $Na_2PdCl_4$, may be used in the practice of this invention.

Phosphines useful in the practice of this invention include monodentate and bidentate phosphines. Non-limiting examples of bidentate phosphines include bis(diphenylphosphino)methane (dppm), 1,2-bis(diphenylphosphino)ethane (dppe), 1,3-bis(diphenylphosphino) propane (dppp), and 1,4-bis(diphenylphosphino)butane (dppb). Non-limiting examples of monodentate phosphines include $P(C_6H_{11})_3$, $P(n-C_4H_9)_3$, $P(p-CH_3OC_6H_5)_3$, $P(p-tolyl)_3$, $P(m-tolyl)_3$ and $P(CH_2CH_2CN)_3$.

Other forms of palladium, such as a preformed palladium complex may be used in the practice of this invention. These include $Pd(C_6H_5CN)_2Cl_2$, $Pd(CH_3CN)_2Cl_2$ and $Pd(PR_3)_2X_2$ wherein R is alkyl or phenyl and X is halide.

The addition of chloride is desirable in the process of the present invention to increase conversion. The chlorine is preferably added in the form of a chloride salt. Examples of suitable salts include NaCl, KCl, LiCl, $MgCl_2$ and $R_4N^+Cl^-$ wherein R is alkyl, preferably $C_{1-4}$ alkyl.

The process of the present invention may be conducted at temperatures and pressures and such other conditions as are necessary to obtain desired yields. The reaction will preferably be conducted at elevated temperatures and pressures. It is preferred that temperatures be greater than about 75° C. and pressures be greater than about 75 psig to obtain reasonable conversions. Upper limits on temperatures and pressures are typically set by economic considerations relating to the cost of equipment and resources to operate at elevated temperatures and pressures. It is generally preferred that these operating conditions are the same as they would be in the absence of the present invention, i.e. the use of an ether solvent to obtain enhanced stereo selectivity.

The process of the present invention may be operated in a batch, semi-batch or continuous manner.

The following examples are provided to illustrate the invention, but should not be considered as limiting it in any way. Unless stated otherwise, all parts and percentages are by weight.

Example 1

A 30 g (0.20 moles) portion of 1,2,3,6-tetrahydrophthalic acid anhydride, 30 g (1.67 moles) water, 0.20 g (0.0011 moles) palladium (II) chloride, 0.60 g (0.0023 moles) triphenylphosphine and 100 ml dioxane are loaded into a glass liner in a 600 ml Monel ™ stirred autoclave. The reactor is purged three times with nitrogen at 115 psig, then filled with carbon monoxide (850 psig) and heated to 95° C. The reaction is run for 2000 minutes. The product is derivatized with bis(trimethylsilyl)trifluoroacetamide and then analyzed by gas chromatography. Conversion is over 99 percent and selectivity to cis-1,2,-trans-4-cyclohexanetricarboxylic acid is 80 percent.

Example 2

A 20 g portion of 1,2,3,6-tetrahydrophthalic acid anhydride, 20 g water, 0.20 g palladium (II) chloride, 0.60 g triphenylphosphine and 120 ml of solvent are loaded into a glass liner in a 600 ml Monel TM stirred autoclave. The reactor is purged three times with nitrogen at 115 psig, then filled with carbon monoxide (1050 psig) and heated to 95° C. The reaction is run for 600 minutes. The product is derivatized with bis(trimethylsilyl)trifluoroacetamide and then analyzed by gas chromatography. The identity of the solvent is varied and the percentage selectivity to cis-1,2,-trans-4-cyclohexanetricarboxylic acid obtained are shown in Table I below.

TABLE I

|  |  |
| --- | --- |
| Tetrahydopyran | 75.4 |
| bis(2-ethyoxyethyl)ether[1] | 71 |
| diethyl ether | 71.7 |
| tetrahydrofuran | 75.7 |
| dioxane | 79.4 |
| bis(2-methyoxyethyl)ether[2] | 72.0 |
| ethylene glycol diethyl ether | 78.3 |

[1]Additionally, 1 ml of 37 percent HCl was added.
[2]Conducted at 110° C. rather than 95° C.

Example 3

The procedure set forth in Example 2 is followed with the exception that the identity of the phosphine is varied as shown in Table II below.

TABLE II

|  |  |
| --- | --- |
| DPPE[1] | 68 |
| DPPP[2] | 81 |
| DPPB[3] | 59 |
| $P(C_6H_{11})_3$ | 81 |
| $P(Bu)_3$ | 64 |

[1]DPPE is bis-(diphenylphosphino)ethane.
[2]DPPP is 1,3-bis-(diphenylphosphino)propane.
[3]DPPB is 1,4-bis-(diphenylphosphino)butane.

WHAT IS CLAIMED IS:

1. A process for preparing cis-1,2-trans-4-cyclohexane tricarboxylic acids and esters thereof comprising contacting carbon monoxide, a first reagent selected from the group consisting of cis-1,2,3,6-tetrahydrophthalic acid, cis-1,2,3,6-tetrahydrophthalic acid ester, cis-1,2,3,6-tetrahydrophthalic acid anhydride and mixtures thereof, and a second reagent selected from the group consisting of water, lower alkanols and mixtures thereof in the presence of a palladium complex and an ether solvent at elevated pressure and temperature and such other reaction conditions necessary to result in the formation of the desired cis-trans isomer.

2. The process of claim 1 wherein the ether solvent is selected from the group consisting of dioxane, tetrahydropyran, bis(2-methoxyethyl) ether, bis(2-ethoxyethyl) ether, diethyl ether, ethylene glycol diethyl ether and tetrahydrofuran.

3. The process of claim 1 wherein the carbon monoxide, first reagent and second reagent are contacted in the further presence of a chloride salt.

4. The process of claim 1 wherein the second reagent is water.

5. In a process for preparing cis-1,2-trans-4-cyclohexane tricarboxylic acids and esters thereof by contacting carbon monoxide, a first reagent selected from the group consisting of cis-1,2,3,6-tetrahydrophthalic acid, cis-1,2,3,6-tetrahydrophthalic acid ester, cis-1,2,3,6-tetrahydrophthalic acid anhydride and mixtures thereof, and a second reagent selected from the group consisting of water, lower alkanols and mixtures thereof in the presence of a palladium complex, the improvement comprising the use of an ether solvent to increase selectivity to the cis-trans isomer of the desired cyclohexane tricarboxylic product.

6. The process of claim 5 wherein the ether solvent is selected from the group consisting of dioxane, tetrahydropyran, bis(2-methoxyethyl) ether, bis(2-ethoxyethyl) ether, diethyl ether, ethylene glycol diethyl ether and tetrahydrofuran.

* * * * *